US00PP17889P2

(12) United States Plant Patent
Olesen

(10) Patent No.: US PP17,889 P2
(45) Date of Patent: Jul. 31, 2007

(54) **BOTANICAL CLASSIFICATION *ROSA* HYBRID VARIETY DENOMINATION 'POULPAR041'**

(50) Latin Name: ***Rosa* hybrid**
Varietal Denomination: Poulpar041

(75) Inventor: Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 11/337,253

(22) Filed: Jan. 19, 2006

(51) Int. Cl.
*A01H 5/00* (2006.01)

(52) U.S. Cl. ..... Plt./119
(58) Field of Classification Search ..... Plt./119
See application file for complete search history.

*Primary Examiner*—Kent Bell
*Assistant Examiner*—Annette H Para

(57) ABSTRACT

A new miniature rose plant that has abundant, pink apricot blend flowers and attractive foliage. The variety successfully propagates from softwood cuttings and is suitable for year-round production in commercial glasshouses. This new and distinct variety has shown to be uniform and stable in the resulting generations from asexual propagation.

1 Drawing Sheet

Botanical classification: *Rosa* hybrid.
Variety denomination: 'Poulpar041'.

SUMMARY OF THE INVENTION

The present invention constitutes a new and distinct variety of miniature rose plant which originated from a controlled crossing between the female seed parent, an unnamed seedling, and the male pollen parent, 'Korkleiva' described and illustrated in U.S. Plant Pat. No. 11,232. The two parents were crossed, and the resulting seeds were planted in a controlled environment. The new variety is named 'Poulpar041'.

The new variety may be distinguished from its seed parent by the following combination of characteristics:

1. 'Poulpar041' has a flower diameter of 35 to 40 mm while the pollen parent has a smaller diameter of 25 to 30 mm.
2. 'Poulpar041' has pink apricot blend flowers while the pollen parent has near white flowers.

The new rose may be distinguished from its pollen parent 'Korkleiva' by the following combination of characteristics:

1. 'Poulpar041' has normally 35 flower petals, 10 to 13 of which are petaloids. 'KORklevia' has 25 to 30 flower petals.
2. Flower diameter of 'Poulpar041' is 35 to 40 mm, while 'Korklevia' is 38 to 44 mm.

The objective of the hybridization of this rose variety for commercial culture was to create a new and distinct variety with unique qualities, such as:

1. Uniform and abundant pink apricot blend flowers;
2. Vigorous and compact growth;
3. Year-round flowering under glasshouse conditions;
4. Suitability for production from softwood cuttings in 10 to 15 cm pots;
5. Durable flowers and foliage which make a variety suitable for distribution in the floral industry.

This combination of qualities is not present in previously available commercial cultivars of this type, known to the inventor, and distinguish 'Poulpar041' from all other varieties of which we are aware.

As part of the rose development program, Mogens N. Olesen germinated the seeds from the aforementioned hybridization and conducted evaluations on the resulting seedlings in a controlled environment in Fredensborg, Denmark.

'Poulpar041' was selected by the inventor as a single plant from the progeny of the hybridization in June 2002.

Asexual reproduction of 'Poulpar041' by cuttings and traditional budding was first done by Mogens N. Olesen in the nursery in Fredensborg, Denmark in April 2003. This initial and other subsequent propagations conducted in controlled environments have demonstrated that the characteristics of 'Poulpar041' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'Poulpar041'. Specifically illustrated in the drawing:

FIG. 1.1; Flower buds at various stages of opening;

FIG. 1.2; Open flowers, side view and above view;

FIG. 1.3; Sepals detached, and sepals, pedicel, and receptacle showing reproductive flower parts;

FIG. 1.4; Petals, detached;

FIG. 1.5; Juvenile and mature compound leaves;

FIG. 1.6; Juvenile stem, showing juvenile growth, and mature bare stems.

DETAILED DESCRIPTION OF THE VARIETY

The following is a description of 'Poulpar041', as observed in its growth in glasshouses in Odense, Denmark. Observed plants are 4 months of age and were cultivated in 10.5 cm pots. Color references are made using The Royal Horticultural Society (London, England) Colour Chart, 2001, except where common terms of color are used.

For a comparison, several physical characteristics of the rose variety 'Poulpar030', a rose variety from the same inventor, described and illustrated in U.S. Plant Pat. No.

16,855 filed on Dec. 1, 2004, are compared to 'Poulpar041' in Chart 1.

CHART 1

| | 'Poulpar041' | 'Poulpar030' |
|---|---|---|
| Petalage | 35 flower petals, 10 to 13 of which are petaloids | Semi-double; 25 petals. |
| General tonality of flower color | On open flower Red Group 38A to Red Group 41C with intonations of Yellow Group 11A to 11B and Yellow Orange Group 22D. Changes in tonality after flowers have reached peak maturity are apparent. Flowers become Red Group 38A to 38C with intonations of Red Group 36D. | On open flower Yellow-Orange Group 20B with intonations of Orange Group 25B. No change in the general tonality at the end of the 10th day. Afterwards, general tonality is Orange Group 27C with intonations of Red Group 36A. |
| Flower diameter | 35 to 40 mm | 60 mm |

FLOWER AND FLOWER BUD

Blooming habit: Continuous.

Flower bud:

*Size.*—Upon opening, 20 mm in length from base of receptacle to end of bud. Average diameter is 9 mm.

*Bud form.*—Pointed ovate.

*Bud color.*—As sepals unfold, new petals are Orange Group 27A blended with light intonations of Yellow Group 10 C. Petal margins are Red Group 37C to Red Group 38A.

*Sepals.*—Upper Surface: Color: The inner surfaces of sepals are Yellow-Green Group 144B to 144C with strong anthocyianic pigments of Greyed-Orange Group 176A located towards the sepal apex. Pubescence: Medium. Lower Surface: Color: Yellow-Green Group 146B, with strong anthocyanic intonations the color of Greyed-Red Group 176A. Texture: Rough with many stipitate glands. Shape: Sepal shape is cirrhose. Base is flat at union with receptacle. Size: Normally 18 to 23 mm in length, by 8 to 10 mm wide. Margins: Margins have strong foliaceous appendages. Stipitate glands are abundant.

*Receptacle.*—Surface Texture: Smooth. Shape: Funnel shaped. Size: 3 mm (h)×5 mm (w). Color: Yellow-Green Group 146B to 144A with anothocyanic pigments the color of Greyed-Orange Group 166A.

*Pedicel.*—Surface: Somewhat rough with stipitate glands. Length: Normally 24 to 32 mm. Diameter: 3 mm on average. Color: Yellow-Green Group 146B to Yellow-Green Group 144A. Strong anthocyanic pigments the color of Greyed-Orange Group 166A observed. Strength: Strong, erect.

*Borne.*—Normally singularly or in clusters of 2 to 3 buds per flowering stem.

Flower bloom:

*Fragrance.*—Light floral scent.

*Duration.*—As a potted plant, flowers last 14 to 21 days. Petals do not fall cleanly away from plant after reaching full maturity.

*Size.*—Flower diameter is normally 35 to 40 mm. Average flower depth is 20 mm when open.

*Form.*—Generally, the central petals remain somewhat tightly closed, while outer petal open and reflex outward.

*Shape of flower.*—When viewed from the side: Upon opening: Upper part is a flattened convex. Lower part is flat. Open flower; Upper part is convex. Lower part is concave to flat.

*Petalage.*—Thre are normally 35 petals, 10 to 13 of which are petaloids.

Flowers:

*Petal color.*—The upper surface coloration is Red Group 37B blended with Orange-Red Group 32C and 32D at the margins. The middle zone coloration is Yellow Group 10A. The lower surface coloration is generally Orange Group 24C with intonations of Yellow 10C at the middle zone. Distinct coloration at the base of the upper and lower petal surfaces is Yellow-Green Group 154C.

*General tonality.*—On open flower Red Group 38A to Red Group 41C with intonations of Yellow Group 11A to 11B and Yellow Orange Group 22D. Changes in tonality after flowers have reached peak maturity are apparent. Flowers become Red Group 38A to 38C with intonations of Red Group 36D.

Petals:

*Petal reflex.*—Reflexed.

*Petal margin.*—Entire and occasionally with a point at the center of the petal apex. Medium undulations of margin observed.

*Shape.*—Broad elliptical. Base: Obtuse. Apex: Rounded.

*Size.*—Outer petals: 17 mm (l)×17 mm (w). Inner petals: 15 mm (l)×12 mm (w).

Petaloids:

*Size.*—8 mm (l)×6 mm (w).

*Shape.*—Irregular with cleft at the apex on some petaloids.

*Color.*—Upper surface: Margins are Orange-Red Group 30A, blending with Yellow Group 10B at mid zone. Basal petal spot is Yellow-Green Group 154C. Lower Surface: Orange Group 29B with light intonations of Yellow Group 11C. Basal petal spot is Yellow-Green Group 154C.

Reproductive organs:

*Pollen.*—None observed.

*Anthers.*—Size: 2 mm long. Color: Yellow-Orange Group 20A. Quantity: 55 to 60.

*Filaments.*—Color: Yellow Group 1C. Length: 2 mm.

*Pistils.*—Length: 3 mm. Quantity: 70 to 75.

*Stigmas.*—Inferior in location relative to the length of the filaments and the height of the anthers. Color: Greyed-Yellow Group 161D.

*Styles.*—Color: Red Group 50A.

*Seed formation.*—Not observed.

PLANT

Plant growth: Upright and moderately bushy. When grown as a 10.5 cm pot plant on its own roots, the average height of the plant itself is 20 to 25 cm. Average spread is 15 to 20 cm.

Stems:

*Color.*—Juvenile growth: Yellow-Green Group 146C. Occasionally, intonations of Greyed-Purple Group 183D observed. Mature growth: Yellow-Green Group 146B to 146C. Occasionally, intonations of Greyed-Purple Group 183D observed.

*Internodal distance.*—20 mm.

*Length of stems.*—On average stems are 15 cm from the base of the plant to the flowering portion.

*Diameter.*—Normally 4 mm.

*Surface texture.*—Young wood: Smooth to somewhat rough with stipitate glands. Older wood: Rough with small prickles.

Prickles:

*Incidence.*—Average 10 prickles per 10 cm of stem.

*Size.*—Average prickle length is 2 mm.

*Color.*—Juvenile: Greyed-Red Group 182 to Yellow-Green Group 144C. Mature: Greyed-Yellow Group 162A.

*Shape.*—Upper side: Flat. Lower side: Flat.

Plant foliage: Compound leaves, found at mid stem normally consist of 7 leaflets.

*Compound leaf size.*—70 to 90 mm (l)×40 to 50 mm (w).

*Quantity.*—5 leaves per 10 cm of stem.

*Color of juvenile foliage.*—Upper Surface: Yellow-Green Group 144B. Anthocyanic intonations of Greyed-Purple Group 185A observed at leaflet margins. Lower Surface: Yellow-Green Group 144C to 146D.

*Color of mature foliage.*—

*Upper leaf surface.*—Green Group 137A.

*Lower leaf surface.*—Yellow-Green Group 147C to 147D.

Plants leaves and leaflets:

*Stipules.*—Size: 9 mm in length. Shape: Linear, slightly broad based with outward extending apecies. Margins: Finely serrated with stipitate glands. Color: Green Group 143A.

*Petiole.*—Length: 14 mm. Diameter: 1.25 mm. Petiole Color: Upper surface: Green Group 143A with Greyed-Red Group 182C. Lower surface: Yellow-Green Group 144A.

*Rachis.*—Size: 35 to 45 mm. Rachis Color: Upper surface: Yellow-Green Group 144A with strong anthocyanic intonations of Greyed-Red Group 178A. Lower surface: Yellow-Green Group 144A. Underneath: Few stipitate glands present. Few small prickles observed.

*Leaflet.*—Size: Normally 25 to 30 mm in length by 18 to 20 mm wide. Margin: Serrated to doubly serrated. General Shape: Elliptical to somewhat cordate. Apex Shape: Acuminate. Base Shape: Obtuse. Texture: Smooth. Thickness: Average. Arrangement: Odd pinnate. Venation: Reticulate. Leaf Gloss: Slightly glossy.

Disease resistance: Average resistance to powdery and downy mildew, black spot, and *Botrytis* under normal growing conditions in Odense, Denmark.

It is claimed:

1. A new and distinct variety of rose plant of the miniature class named 'Poulpar041', substantially as illustrated and described herein, due to its abundant, pink apricot blend flowers, vigorous growth, compact habit, suitability for production from softwood cuttings in small pots, and durable flowers and foliage that make the variety suitable for distribution in the floral industry.

* * * * *

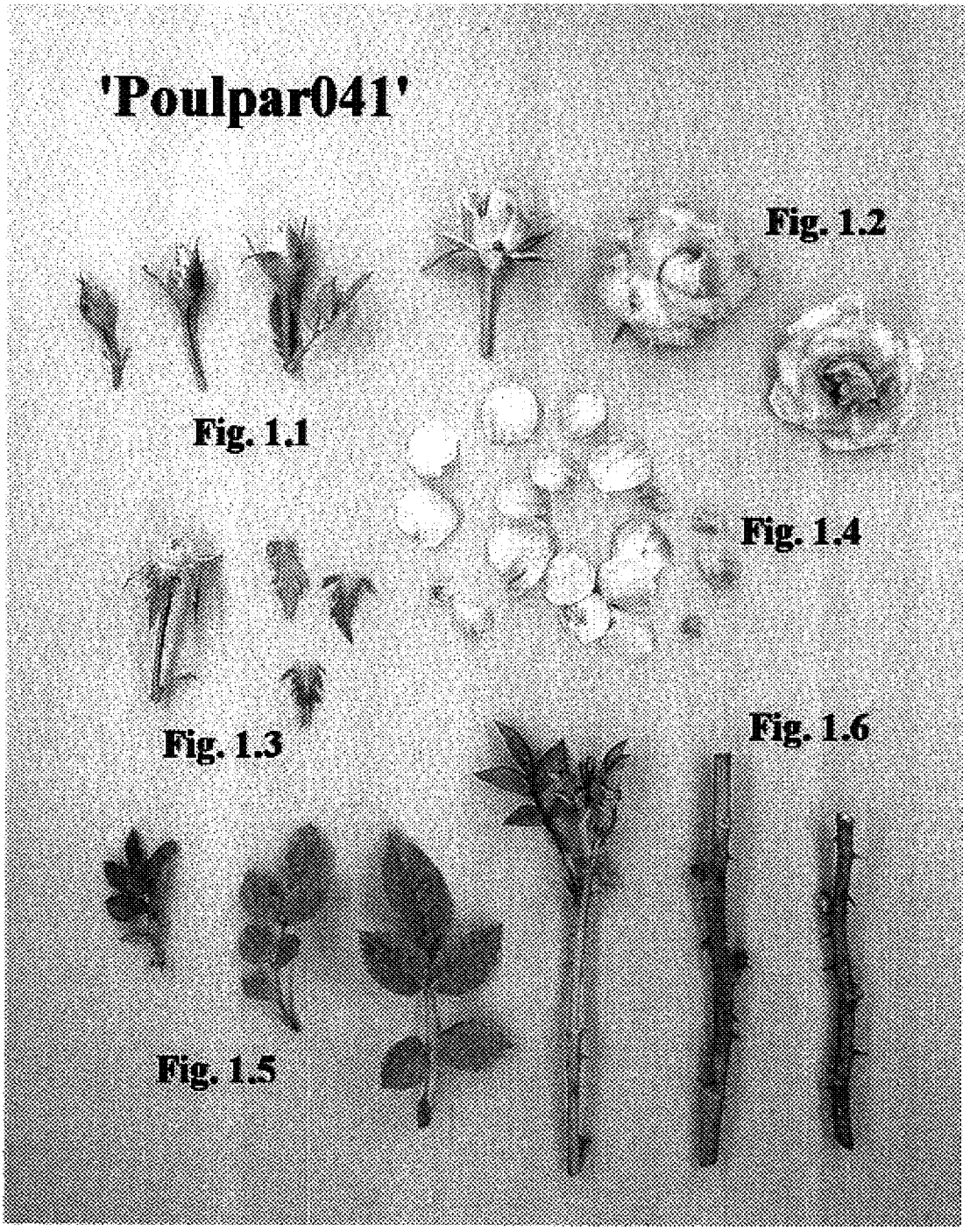
'Poulpar041'
Fig. 1.1
Fig. 1.2
Fig. 1.3
Fig. 1.4
Fig. 1.5
Fig. 1.6